(12) United States Patent
Richter (10) Patent No.: US 11,508,470 B2
(45) Date of Patent: Nov. 22, 2022

(54) ELECTRONIC MEDICAL DATA TRACKING SYSTEM

(71) Applicant: Medos International Sarl, Le Locle (CH)

(72) Inventor: Joern Richter, Kandern (DE)

(73) Assignee: Medos International Sarl

(*) Notice: Subject to any disclaimer, the term of this patent is extended or adjusted under 35 U.S.C. 154(b) by 654 days.

(21) Appl. No.: 16/430,912

(22) Filed: Jun. 4, 2019

(65) Prior Publication Data

US 2020/0388361 A1 Dec. 10, 2020

(51) Int. Cl.
  *G16H 10/65* (2018.01)
  *G07C 9/25* (2020.01)

(52) U.S. Cl.
  CPC ............. *G16H 10/65* (2018.01); *G07C 9/257* (2020.01)

(58) Field of Classification Search
  CPC ........ G16H 10/65; G16H 80/00; G16H 40/67; G07C 9/257
  See application file for complete search history.

(56) References Cited

U.S. PATENT DOCUMENTS

| | | | |
|---|---|---|---|
| 6,392,546 B1 | 5/2002 | Smith | |
| 6,711,414 B1 | 3/2004 | Lightman et al. | |
| 6,954,148 B2 | 10/2005 | Pulkkinen et al. | |
| 7,039,221 B1* | 5/2006 | Tumey | G07C 9/37 |
| | | | 382/118 |
| 7,103,379 B2 | 9/2006 | Hilerio | |
| 7,496,479 B2 | 2/2009 | Garcia et al. | |
| 8,041,582 B2 | 10/2011 | Godschall et al. | |
| 8,237,558 B2 | 8/2012 | Seyed Momen et al. | |
| 9,135,805 B2 | 9/2015 | Freedman et al. | |
| 9,147,334 B2 | 9/2015 | Long et al. | |
| 9,235,977 B2 | 1/2016 | Deutsch | |
| 9,524,530 B2 | 12/2016 | Moharir | |
| 9,564,038 B2 | 2/2017 | Wallace et al. | |
| 11,069,220 B2* | 7/2021 | Wittrup ............... | G08B 21/245 |
| 2005/0149358 A1 | 7/2005 | Sacco et al. | |
| 2006/0000895 A1* | 1/2006 | Bonalle .................. | G06F 21/34 |
| | | | 235/382 |
| 2007/0043637 A1 | 2/2007 | Garcia et al. | |
| 2008/0164998 A1 | 7/2008 | Scherpbier et al. | |
| 2009/0106692 A1 | 4/2009 | Bhavani | |

(Continued)

FOREIGN PATENT DOCUMENTS

| | | |
|---|---|---|
| KR | 10-1686822 B1 | 12/2016 |
| WO | 2010/099488 A1 | 9/2010 |

(Continued)

*Primary Examiner* — Robert A Sorey
(74) *Attorney, Agent, or Firm* — BakerHostetler (57) ABSTRACT

Techniques for addressing various technical problems associated with managing medical data are described herein. One or more medical data tracking applications can execute on an electronic medical data tracking system. Such a computer system can include one more computing devices, such as for example a mobile computing device and a central computing system, that can optionally communicate with each other to send and receive information associated with a patient. The mobile computing device can be configured as an employee identification card, and can be configured to detect and identify patients, gestures, medical devices, and medicine associated with medical procedures.

18 Claims, 4 Drawing Sheets

(56) References Cited

U.S. PATENT DOCUMENTS

| | | | |
|---|---|---|---|
| 2012/0026308 A1* | 2/2012 | Johnson | H04N 7/18 |
| | | | 348/E7.085 |
| 2013/0093829 A1 | 4/2013 | Rosenblatt et al. | |
| 2013/0339039 A1 | 12/2013 | Román et al. | |
| 2014/0200937 A1 | 7/2014 | Friedman | |
| 2014/0204190 A1* | 7/2014 | Rosenblatt, III | G16H 70/20 |
| | | | 705/2 |
| 2014/0222462 A1 | 8/2014 | Shakil et al. | |
| 2014/0249891 A1 | 9/2014 | Olguin Olguin et al. | |
| 2014/0310012 A1* | 10/2014 | Azzaro | G16H 40/20 |
| | | | 705/2 |
| 2015/0127365 A1 | 5/2015 | Rizvi et al. | |
| 2015/0213206 A1 | 7/2015 | Amarasingham et al. | |
| 2015/0324528 A1 | 11/2015 | Chang | |
| 2016/0078180 A1 | 3/2016 | Stackpole et al. | |
| 2016/0125348 A1* | 5/2016 | Dyer | H04W 4/33 |
| | | | 705/7.42 |
| 2017/0039423 A1* | 2/2017 | Cork | G06F 3/167 |
| 2017/0124836 A1 | 5/2017 | Chung et al. | |
| 2017/0232300 A1 | 8/2017 | Tran et al. | |
| 2017/0235897 A1 | 8/2017 | Henderson et al. | |
| 2018/0114288 A1* | 4/2018 | Aldaz | G16H 10/65 |

FOREIGN PATENT DOCUMENTS

| | | | |
|---|---|---|---|
| WO | 2011/058292 A1 | 5/2011 | |
| WO | 2014/062714 A1 | 4/2014 | |
| WO | 2015/193736 A2 | 12/2015 | |
| WO | 2017/062621 A1 | 4/2017 | |
| WO | 2017/075541 A1 | 5/2017 | |
| WO | 2017/094016 A1 | 6/2017 | |
| WO | WO-2020038445 A1 * | 2/2020 | G02B 7/182 |

\* cited by examiner

ELECTRONIC MEDICAL DATA TRACKING SYSTEM

BACKGROUND

It is estimated that a nurse or other medical professional may expend approximately 30 to 40 percent of his or her time manually updating patients' medical records to reflect the medical care administered to his or her patients. In some cases, manually entering data into patients' medical records can result in costly errors. Further, manually entering data into patients' medical records expends time that could otherwise be used to care for patients. Thus, reducing the amount of time that a medical professional expends on updating medical records could increase the amount of time that the medical professional could expend caring for a particular patient and/or result in an increase in the number of patients that can be cared for by a given medical professional over time.

SUMMARY

In an example embodiment, an employee identification card comprises a card-shaped body that supports an employee identifier, sensor system, and an output device. The employee identifier identifies an employee associated with the employee identification card. The sensor system is configured to detect a motion that is characteristic of a medical procedure administered to a patient and generate motion characteristic data that characterizes the medical procedure. The output device is configured to output the motion characteristic data to a central computing system that is configured to update a medical record of the patient to reflect that the procedure was administered to the patient.

In another example embodiment, an electronic medical data tracking system comprises a mobile computing device and a central computing system that is in communication with the mobile computing device. The mobile computing device comprises a sensor system configured to detect a motion that is characteristic of a medical procedure administered to a patient and generate motion characteristic data that characterizes the medical procedure. The central computing system comprises a processor, and memory in communication with the processor. The memory has a database of patient records stored therein and instructions that, upon execution by the processor, cause the central computing system to identify a medical record associated with the patient from the database of patient records, and update the medical record associated with the patient in the database to reflect that the medical procedure has been administered to the patient.

In yet another example embodiment, a computer-implemented method comprises a step of causing a sensor system of a mobile computing device to detect a motion that is characteristic of a medical procedure administered to a patient to generate motion characteristic data that characterizes the medical procedure. The method comprises causing the mobile computing device to communicate the motion characteristic data to a central computing system. The method comprises causing the central computing system to identify a medical record associated with the patient from a database of patient records stored in memory of the central computing system. The method comprises causing the central computing system to update the medical record associated with the patient in the database to reflect that the medical procedure has been administered to the patient.

The foregoing summarizes only a few aspects of the present disclosure and is not intended to be reflective of the full scope of the present disclosure. Additional features and advantages of the disclosure are set forth in the following description, may be apparent from the description, or may be learned by practicing the invention. Moreover, both the foregoing summary and following detailed description are exemplary and explanatory and are intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings.

DETAILED DESCRIPTION OF ILLUSTRATIVE EMBODIMENTS

Various embodiments of the disclosure relate to devices, systems, and methods for the automated detection of a medical procedure administered to a patient and the updating of the patient's medical records to reflect that the detected medical procedure has been administered. The medical procedure is detected using a mobile computing device, which, in at least some embodiments, can be implemented in a medical employee identification card or nametag. In some embodiments, the mobile computing device can be configured to communicate with a central computing system or network of computing devices that stores the patient's records in for, example, a database.

Figure 1:
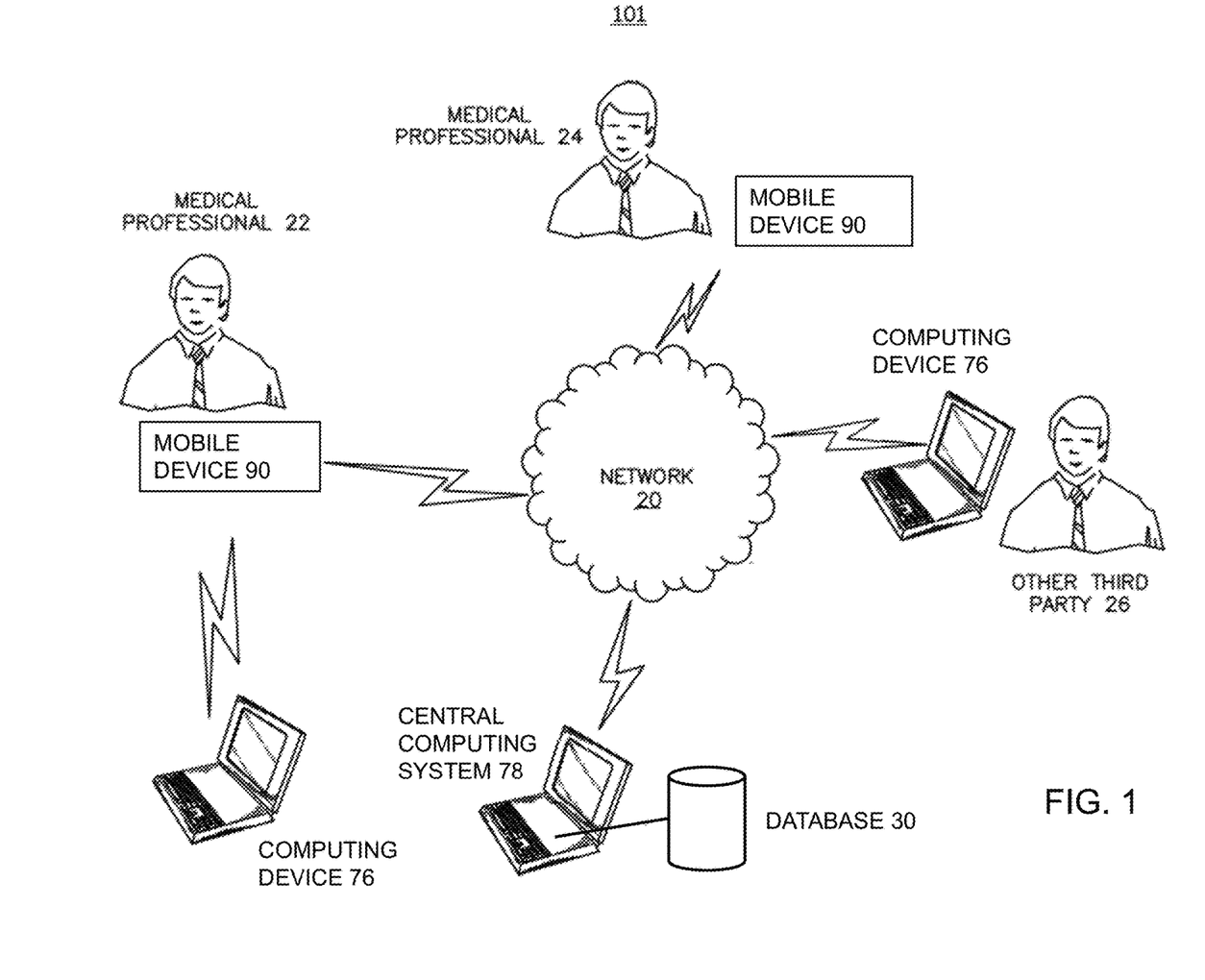
FIG. 1 is an example communication architecture or electronic medical data tracking system for use in accordance with the present disclosure.

Referring to FIG. 1, one example of a communication architecture or electronic medical data tracking system 101 is shown. It will be appreciated that numerous suitable alternative communication architectures are envisioned. The system 101 can comprise one or mobile computing devices 90 that are configured to be carried by a medical care professional 22 or 24, such as a nurse or doctor. In some embodiments, each mobile computing device 90 can be a wearable computing device. In a preferred embodiment, each mobile computing device 90 can be implemented as a medical employee identification card (e.g., nametag). However, it will be understood that, in alternative embodiments, each mobile computing device 90 can be implemented as another type of mobile device such as a mobile phone or tablet. Each mobile computing device 90 can be configured to detect at least one of (i) an identifying characteristic of a patient, (ii) administering of a medical procedure administered to the patient, and (iii) a medical device.

Each mobile computing device 90 can be in communication with a central computing system 78 over a common network 20, such as the Internet or an Intranet. The central computing system 78 can be implemented as at least one computing device or a system or network of computing devices. Each computing device of the central computing system 78 can be implemented as, without limitation, a server, a desktop, a laptop, a mobile phone, a tablet computer, or the like. The central computing system 78 can include a database 30 that stores patients' medical records. In some examples, the database 30 can additionally store patient identification information, such as (without limitation) data related to patient faces, fingerprints, or other identification information. In some examples, the database 30 can additionally store motion characteristic data that characterizes a plurality of hand or medical device motions associated with a plurality of medical procedures.

The central computing system 78 can be configured to update a patient's medical records to reflect that a medical procedure has been administered to a patient. Thus, the central computing system 78 can be configured to associate a particular medical procedure detected by a mobile computing device 90 with a particular patient's record stored in the database 30. It will be understood that, in some embodiments, the medical records of a plurality of patients can be stored in a single computing device of the central computing system 78 or across a plurality computing devices of the central computing system 78. Thus, each mobile computing device 90 can be in communication with a single computing device of the central computing system 78 or a plurality of computing devices of the central computing system, each including a database 30 of patients' medical records.

Figure 2:
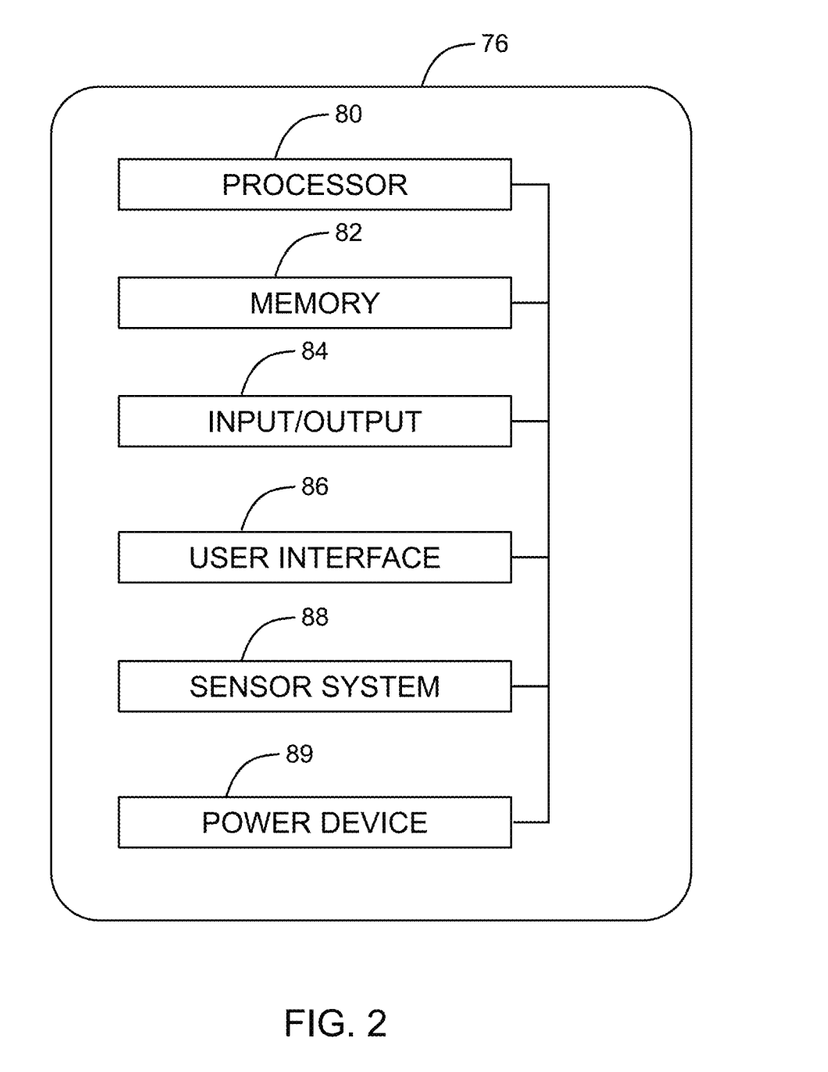
FIG. 2 is a schematic diagram of an example mobile computing device for use in accordance with the present disclosure.

Referring to FIGS. 1 and 2, a suitable computing device 76 such as an example computing device of the central computing system 78 or an example mobile computing device 90, can be configured to host a medical data tracking application. The mobile computing device 90 (shown in FIGS. 1 and 3) can include all or a portion of the computing device 76. Similarly, a computing device of the central computing system 78 (shown in FIG. 1) can include all or a portion of the computing device 76. The medical data tracking application can be a program, such as software or hardware or a combination of both, that can be run on one or more suitable computing devices. It will be appreciated that the embodiments described herein can be applied to track any medical data, for instance any medical processes or records associated with medical inventories or patients. In this regard, reference below to the medical data tracking application can be further construed as an application that can assist in the tracking of data associated with medical procedures, such as the administering of medical devices or medication, or the maintenance of patient records. It will be understood that the computing device 76 can include any appropriate device, examples of which include a desktop computing device, a server computing device, or a portable computing device, such as a laptop, tablet, or smart phone.

In an example configuration, the computing device 76 can include at least one processor 80, a memory 82, an input/output device 84, and a power device 89. In some examples, such as when the computing device 76 implements the mobile computing device 90, the computing device 76 can include a user interface (UI) 86 and a sensor system 88. In an example configuration, referring to FIG. 2, the mobile computing device 90 includes at least one processor 80, the memory 82, the input/output device 84, the user interface 86, the sensor system 88, and the power device 89. It is emphasized that the block diagram depiction of the computing device 76 is exemplary and not intended to imply a specific implementation and/or configuration. The at least one processor 80, memory 82, input/output device 84, user interface 86, and sensor system 88 can be coupled together to allow communications therebetween. As should be appreciated, any of the above components may be distributed across one or more separate devices and/or locations. For example, the mobile computing device 90 can include any, or all of, the processor 80, memory 82, input/output device 84, user interface 86, and the sensor system 88. In some cases, the mobile computing device 90 can be communicatively coupled to the central computing system 78 via their respective input/output devices 84, so that the central computing system 78 can process and/or store data that is sensed or detected by the sensor system 88 of the mobile computing device 90.

In various embodiments, the input/output device 84 includes a receiver of the central computing system 78 or mobile computing device 90, a transmitter of the central computing system 78 or mobile computing device 90, or a combination thereof. The input/output device 84 is capable of communicating, such as receiving and/or transmitting information pertaining to a communications network such as, for example, the Internet or an Intranet. The communications can be over, for example, a wired or wireless communications channel. As should be appreciated, transmit and receive functionality may also be provided by one or more devices external to the central computing system 78 or the mobile computing device 90.

The at least one processor 80 may include a single processor or more than one processor. Depending upon the exact configuration and type of processor, the memory 82 can be volatile (such as some types of RAM), non-volatile (such as ROM, flash memory, hard disk drive, etc.), or a combination thereof. The computing device 76 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the central computing system 78 or the mobile computing device 90. In preferred embodiments, the mobile computing device 90 comprises only memory that comprises memory cells (i.e., electronic circuits that store bits of binary information) such as RAM or ROM so as to limit size and power requirements of the mobile computing device 90. Embodiments that comprise memory such as RAM or ROM can be implemented with a smaller battery and/or can have better battery life than comparable embodiments that are implemented with some other types of memory.

The computing device 76, such as when implementing the mobile computing device 90, can comprise the user interface 86 allowing a user to communicate with the computing device 76. The user interface 86 can include inputs that provide the ability to control the computing device 76, via, for example, buttons, soft keys, a mouse, voice actuated controls, a touch screen, movement of the computing device 76, visual cues (e.g., moving a hand in front of a camera on the mobile computing device 90), audio cues, or the like. The user interface 86 may also include, for example, a scanner for scanning of information such as bar codes, QR codes, and RFID tags. The user interface 86 can provide outputs, including visual information (e.g., via a display or at least one light), audio information (e.g., via speaker), mechanically (e.g., via a vibrating mechanism), or a combination thereof. In preferred embodiments, the mobile computing device 90 is devoid of any video (and in some cases image) displays so as to limit a size and power requirements of the mobile computing device 90. However, in other embodiments, the user interface 86 can include a display, a touch screen, a keyboard, a mouse, an accelerometer, a motion detector, a speaker, a microphone, a camera, a tilt sensor, or any combination thereof. The user interface 86 can include any suitable device for inputting biometric information, such as, for example, fingerprint information, retinal information, voice information, and/or facial characteristic information.

Figure 3:
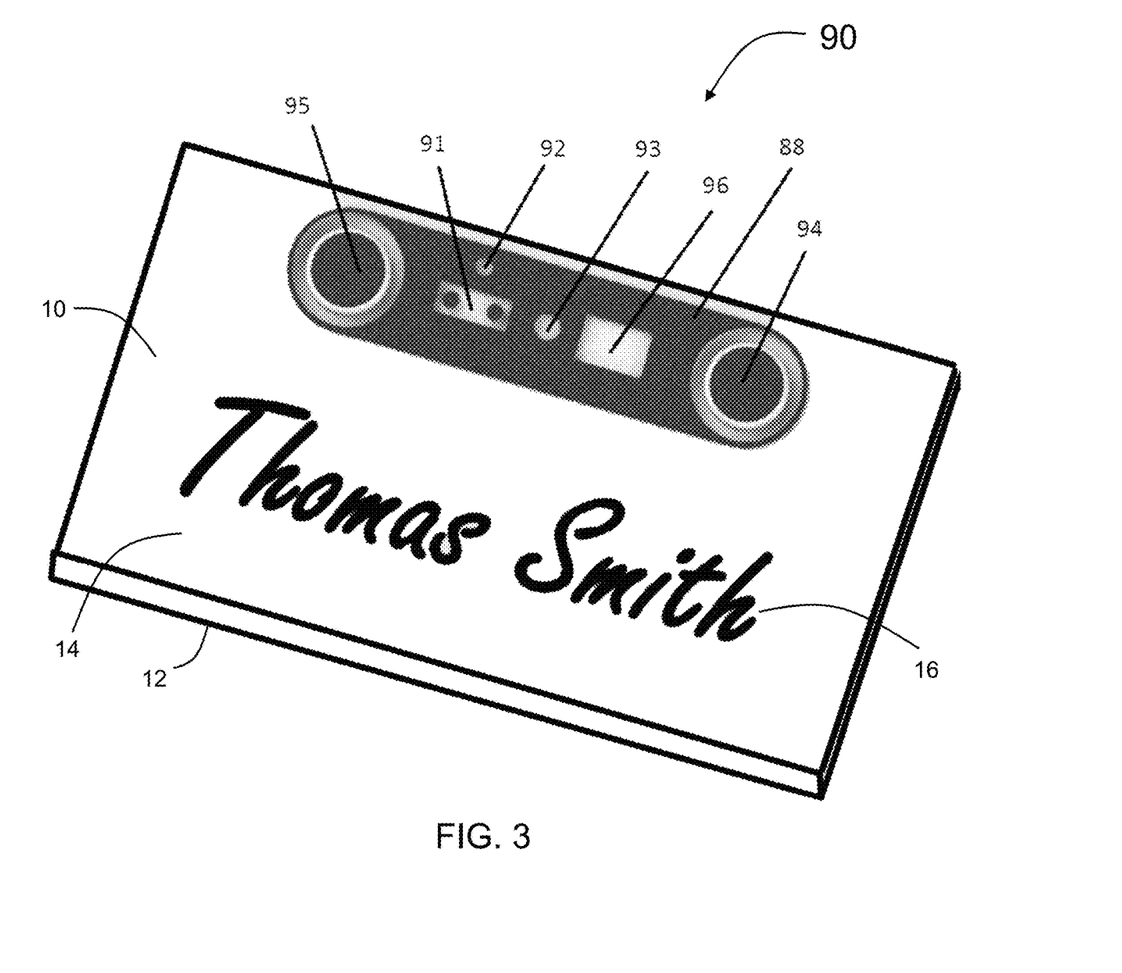
FIG. 3 is a simplified block diagram of an example computing device for use in accordance with the present disclosure.

The computing device 76, such as when implementing the mobile computing device 90, can comprise the sensor system 88, which can include one or more cameras, sensors, or other data capture components. Referring to FIG. 3, by way of example, the sensor system 88 of the mobile computing device 90 can include at least one, up to all, of a proximity sensor 91, an ambient light sensor 92, a speaker and/or microphone 93, a camera 94, an infrared (IR) camera 95, a dot projector 96, and any other suitable sensor. Additionally, or alternatively, the user interface 86 can include at least one of the camera 94, speaker and/or microphone 93, and the dot projector 96. The sensor system 88 can be in communication with a processor of at least one of the central computing system 78 and the mobile computing device 90. The sensor system 88 can be configured to detect motion and physical objects, such as patients or medical instruments, associated with medical procedures, among other motions and objects.

With continued reference to FIG. 3, in an example, the mobile computing device 90 can be a medical employee identification card or nametag that is configured to identify and authenticate a particular medical employee, although various embodiments are not limited to being an identification card. The identification card can be an access card that is configured to provide the particular medical employee with secure access to physical and virtual locations. When the access card is read by a reader, the reader can grant access to the medical employee to a particular physical or virtual location. For example, the mobile computing device 90 can be contact-type card that grants access to a location when the card is in contact with a card reader. As another example, the mobile computing device 90 can be a contactless-type access card, such as a smart card or RFID card, that grants access to a location when the card is in proximity (e.g., within two feet of) to a card reader.

The mobile computing device 90 can comprise an employee identifier that is configured to identify the medical employee. The employee identifier can be configured to be read by a reader such as a card reader. For example, a contact-type card can include an employee identifier that is a machine-readable access code such as a two- or three-dimensional barcode or a magnetic stripe that grants access to a location when the machine-readable access code is in contact with a card reader. As another example, a contactless-type card can include an employee identifier that is a machine-readable access code such as an RFID tag or a code stored by an integrated circuit of the mobile computing device 90. As yet another example, the employee identifier can be a MAC address associated with the mobile computing device 90. Additionally, or alternatively, the mobile computing device 90 can have a visual identifier that is configured to identify the medical employee. The visual identifier can include at least one of a picture and a name of the employee. Thus, the mobile computing device 90 can be a wearable device configured to identify a user.

The mobile computing device 90 can comprise a body 10. The at least one processor 80, the memory 82, the input/output device 84, the user interface 86, and sensor system 88 can be supported by the body 10. In some embodiments, the body 10 can be card-shaped. In some embodiments, the body 10 can have a thickness of no more than 0.4 mm. It will be understood that, in alternative embodiments, the mobile computing device 90 can be implemented as a mobile computing device such as a mobile phone or tablet. The body 10 can have an inner side 12, and an outer side 14 opposite the inner side 12 along an outer direction. The inner side 12 can be configured to face the medical employee when worn by the medical employee.

The mobile computing device 90 can comprise at least one employee identifier 16 supported by the body 10, where the at least one employee identifier identifies an employee associated with the employee identification badge. The employee identifier can be configured as described above. The mobile computing device 90 can comprise the sensor system 88 supported by the body 10 and configured to detect a medical procedure administered by the employee to a patient. For example, each sensor of the sensor system 88 can have a field of view that faces the outer direction so as to face away from the medical employee when the mobile computing device 90 is worn by the employee. The sensor system 88 can be configured to detect motion such as a hand or finger gesture and generate motion characteristic data that characterizes the detected motion.

In some embodiments, the sensor system 88 can comprise a dot projector 96 and an infrared camera 95. The dot projector 96 can be configured to project infrared dots onto an object, such as a face, hand, or medical instrument. The infrared camera 95 can be configured to read a pattern of the dots on the object and generate data that corresponds to discrete points on the object. Detecting discrete points and transmitting the discrete points to the comping system 78 can be less power consuming than recording and transmitting video or still pictures. Further, storing discrete points can require less memory than storing video or still pictures. Accordingly, use of a dot projector 96 can reduce the size requirements of the memory and power source of the mobile computing device 90 over comparable embodiments that rely more heavily on video or still pictures.

The mobile computing device 90 can comprise a power device 89 (shown in FIG. 2). In some embodiments, the power device 89 can be supported by, such as attached to, the body 10. In other embodiments, the power device 89 can be separated from the body 10, and can supply power to the components supported by the body 10 by a wired or wireless connection. The power device 89 is configured to supply power to the sensor system 88 and the processor 80. In at least some examples, the power device 89 can include a battery. Additionally, or alternatively, the power device 89 can include an energy harvesting device configured to capture energy from a suitable energy source that is separate from the sensor system 88. For example, the energy source can be radio waves communicated from an external wireless communicator. Additionally, or alternatively, the power device 89 can capture energy from the medical employee's body itself or from another external source such as a source external to the employee's body. For example, the energy source can include (without limitation) kinetic energy, electric fields, magnetic fields, and so on.

The mobile computing device 90 can comprise an output 84 supported by the body 10, such as a transmitter, that is configured to output the motion characteristic data to a central computing system 78 that is configured to update a medical record of the patient to reflect that the procedure was administered to the patient. In some embodiments, the mobile computing device 90 can comprise a processor 80 (shown in FIG. 2) supported by the body 10. The processor 80 can be configured to associate the motion characteristic data with at least one of a time and a duration, and the output 84 is configured to output the data to the computing device with the at least one of the time and duration. Additionally, or alternatively, the processor 80 can be configured to associate the motion characteristic data with a patient identifier that identifies the patient so that the medical procedure associated with the detected motion can be matched with the patient's medical records.

The processor 80 of the mobile computing device 90 can be configured to analyze the motion characteristic data by comparing the data to a plurality of motions, such as a plurality of hand or finger gestures, to determine which medical procedure was performed by the detected motion. In alternative embodiments, the mobile computing device 90 can be configured to output the motion characteristic data to the central computing system 78, without determining which medical procedure was performed by the detected motion, and the processor 80 central computing system 78 can be configured to analyze the motion characteristic data by comparing the data to a plurality of motions, such as a plurality of hand or finger gestures, to determine which medical procedure was performed by the detected motion.

Referring back to FIG. 1, once one or more medical data tracking applications have been installed onto a computer system 76 including, for example, the central computing system 78 and/or the mobile computing device 90 such as described above, information may be transferred between the mobile computing device 90 and the computing device 78 on a common network 20, such as, for example, the Internet or an Intranet.

In an example configuration, a first user or medical professional 22, such as a technician or nurse, can perform a motion, such as a hand or finger gesture, that is associated with a medical procedure or task. The medical professional 22 can wear the mobile computing device 90, such that the motion is within a field of view of the sensor system 88 of the mobile computing device 90, so that the sensor system 88 can detect the motion. In an example, the sensor system 88, such as a dot projector 96 of the sensor system 88, can be configured to detect motion or gestures associated with medical procedures. The at least one processor 80 of the mobile computing device 90, another computing device 76, or the central computing system 78 can make a comparison, for instance a first comparison, of the detected motion to a plurality of gestures associated with medical procedures. The plurality of gestures can be stored in the database 30 of the central computing system 78 or can otherwise be retrieved from memory. Based on the comparison, the at least one processor 80 can identify a medical procedure that is performed by the motion that was detected. Accordingly, the central computing system 78, and hence the system 101, can update a patient record, for instance a patient record that is stored in the database 30, so as to indicate that the identified medical procedure was performed. In doing so, without being by theory, medical data can be tracked, and medical records can be updated efficiently, thereby enabling the medical profession to focus on performing medical care rather than keeping records of the procedures that they perform.

The sensor system 88 can be configured to detect at least one of (i) an identifying characteristic of a patient, such as facial or fingerprint data, (ii) administering of a medical procedure by a medical professional 22 to a patient, and (iii) a medical device, such as an instrument, implant, or medication. In some examples, the medical procedure can be detected based on a movement of the medical professional 22, such as a hand or finger gesture of the medical professional. In an example, the dot projector 96 can detect a face of a patient and/or detect a movement of the medical professional 22 or medical instrument as the medical professional 22 performs a medical procedure. In some examples, the sensor system 88 can perform continuous sensing to detect a face and/or track movement. In other examples, the sensor system 88 can be selectively activated to detect a face and/or track movement. For example, the sensor system 88 can be activated by the medical professional 22 engaging the sensor system 88 or an input 84 of the mobile computing device 90. The input 84 can be, without limitation, a switch that is engaged by the medical professional 22, a speaker or microphone that receives an audio instruction from the medical professional 22, a camera that detects a hand gesture of the medical professional 22, or an ambient light sensor that detects a change in light. In some examples, the sensor system 88 can be configured to remain active for a select period of time after a patient is identified.

Medical procedures can involve a hand movement that is specific to a given medical procedure. Thus, a plurality of hand gestures that are each representative of a particular medical procedure can be stored in the memory 82 of the central computing system 78, such as in the database 30, or in the memory 82 of the mobile computing device 90. When a hand motion is detected by the sensor system 88, such as by a dot projector 96, the at least one processor 80 of the mobile computing device 90, another mobile computing device 76, or the central computing system 78 can compare the detected hand motion to the plurality of hand gestures to determine which medical procedure was performed by the detected hand motion. If the hand motion matches one of the hand gestures of the plurality of the hand gestures in the memory 82, then at least one processor 80 of the mobile computing device 90, another computing device 76, or the central computing system 78 can identify the medical procedure performed. Example medical procedures that involve specific hand gestures, and thus example medical procedures that can be identified by the medical data tracking system 101, include (without limitation) injecting medication with a syringe, withdrawing blood from the patient, giving medication orally, changing cloth on a medical bed, checking or adjusting various machines, serving food, or the like. In one example, the gestures can be detected by detecting the absolute position of the fingers during a given hand motion. The sensory system 88 can also be configured to detect movement of a patient, for example, from one department (e.g., physiotherapy, radiology, cardiology, etc.) to the next.

Additionally, or alternatively, a microphone 93 of the mobile computing device 90 can receive spoken word discussing a medical procedure administered to a patient. At least one processor 80 of the mobile computing device 90, another computing device 76, or the central computing system 78 can analyze the spoken word using speech recognition to identify the particular medical procedure administered. For instance, a mobile phone within the system 101 could receive the data of the spoken word and/or hand gestures from the mobile computing device 90, and analyze the data to determine a medical procedure administered to a patient.

Patient characterization data, such as (without limitation) data related to patient faces, fingerprints, or other identification information, can be stored in the memory 82 of at least one of the mobile computing device 90 and the central computing system 78 (e.g., in database 30). When an identifying characteristic of a patient is detected by the sensor system 88, the central computing system or the mobile computing device can perform operations comprising (1) comparing the identifying characteristic to a plurality of stored identifying characteristics that are stored in the memory 82 of the central computing system 87 or the mobile computing device 90, and (2) identifying the patient based on the comparison.

For example, facial data related to faces of patients can be stored in the memory 82. When a patient's face is detected by the sensor system 88 of the mobile computing device 90, the mobile computing device 90, another computing device 76, or the central computing system 78, and thus the system 101, can make a comparison, for instance a second comparison, of the detected facial data of the patient to the facial data stored in the memory 82. If the detected facial data of the patient matches facial data associated with one of the faces of the facial data in the memory 82, then the mobile computing device 90, another computing device 76, or the central computing system 78 can determine a patient identifier that identifies the patient.

Thus, based on the comparison, the mobile computing device 90, another computing device 76, or the central computing system 78 can determine a patient identifier associated with the patient. For example, the facial data stored in the memory 82 for the plurality of faces can each be associated with a patient identifier. The identifier can be a name, a number, or any combination of letters and numbers that provides a unique identification for the patient. In some instances, the facial data itself can at least partially define the patient identifier. The patient record that is updated can be associated with the identifier, so that the appropriate patient record is updated. The update may indicate a medical procedure that was performed. For example, the update may indicate that medication was administered or a diagnostic check was performed. Example diagnostic checks that can be performed and detected include, without limitation, blood pressure readings and blood drawings.

As another example, fingerprint data related to fingerprints of patients can be stored in the memory 82 of at least one of the mobile computing device 90 and the central computing system 78. The patient's finger can be aligned with the sensor system 88 of the mobile computing device 90 so as to detect a fingerprint of the patient. The mobile computing device 90, another computing device 76, or the central computing system 78, and thus the system 101, can make a comparison of the fingerprint of the patient to fingerprint data related to a plurality of fingerprints stored in the memory 82. If the fingerprint of the patient matches data associated with one of the patients in the memory 82, then the mobile computing device 90, another computing device 76, or the central computing system 78 determines a patient identifier for the patient. In some examples, the fingerprint data itself can at least partially define the patient identifier.

As yet another example, the patient's identification bracelet can be aligned with the sensor system 88 of the mobile computing device 90 so as to detect a feature of the bracelet such as a bar code or a name of the patient. The mobile computing device 90, another computing device 76, or the central computing system 78, and thus the system 101, can make a comparison of the feature of the bracelet to a plurality of features stored in the memory 82. If the feature of the bracelet matches data associated with one of the patients in the memory 82, then the mobile computing device 90, another computing device 76, or the central computing system 78 determines a patient identifier for the patient. In some examples, the bracelet feature itself can at least partially define the patient identifier.

Data related to medicine, medical instruments, and even nutrition information such as food and drink can be stored in the memory 82 of at least one of the mobile computing device 90 and the central computing system 78, such as in the database 30. For instance, inventory records related to medicine, medical instruments, and nutrition can be stored in the memory 82, so as to indicate quantities of medicine or medical instruments that are available to a given unit, hospital, or the like at a given time. The sensor system 88 of the mobile computing device 90 can be configured to detect medicine administered in medical procedures. Based on the detected medicine, the mobile computing device 90, another computing device 76, or the central computing system 78, and thus the system 101, can identify the medicine and determine an amount of the medicine administered during the medical procedure. In an example, the sensor system 88 of the mobile computing device 90 can be configured to detect a medicine identifier such as machine-readable code (e.g., a bar code such as a QR code) or a name of the medicine so that the system 101 can identify the medicine. The medicine identifier can identify the medicine, and can also identify a rule set associated with the medicine. For example, the mobile computing device 90, another computing device 76, or the central computing system 78, and thus the system 101, can compare the medicine identifier to medicine identifiers that are stored in memory 82 so as to identify the medicine the corresponds to the detected medicine identifier. The rule set associated with the given medicine may indicate recommended dosages for the medicine or instructions for administering the medicine. Alternatively, or additionally, the mobile computing device 90, for example the dot projector 96, can detect the medicine based on the shape or other physical characteristics of the container housing the medicine. In such a configuration, the mobile computing device 90, another computing device 76, or the central computing system 78, and hence the system 101, can compare the shape or other physical characteristics of the container housing the medicine to stored shapes or the physical characteristics of the container housing or of the dosage form so as to identify the medicine that corresponds to the detected shape or physical characteristic. Food given to a patient can be detected in a similar manner.

In some embodiments, the mobile computing device 90 can be configured to give a warning to the medical professional when a detected medicine or food should not be given to a patient. For example, the mobile computing device 90 can detect the medication as discussed above. The mobile computing device 90, another computing device 76, or the central computing system 78, and thus the system 101, can look up the detected medicine in the memory 82, such as in the database 30. If the medicine has already been given within a prescribed time, the medicine the patient has an adverse reaction to the medicine, or the medicine interacts negatively with another medicine given to the patient, then the mobile computing device 90 can give a warning, such as an audible or visual warning, to the medical professional so as to warn the medical professional to not give the medicine.

The mobile computing device 90, another computing device 76, or the central computing system 78, and hence the system 101, can update an inventory record stored in the memory 82, such as the database 30, to indicate the amount of medicine administered. In response to updating the inventory record to indicate the amount of medicine administered, the at least one processor 80 of the mobile computing device 90, another computing device 76, or the central computing system 78 can determine an amount of the medicine in the inventory. The at least one processor 80 of the mobile computing device 90, another computing device 76, or the central computing system 78 can compare the amount of the medicine in inventory to a predetermined threshold. The predetermined threshold can be set as desired. In an example, the predetermined threshold is set so as to represent an amount of medicine that triggers the medicine to be re-stocked. When the amount of medicine in inventory is below the predetermined threshold, the mobile computing device 90, another computing device 76, or the central computing system 78 can send a request for delivery of the medicine so as to increase the amount of medicine in inventory above the predetermined threshold. Referring to FIG. 2, for example, the mobile computing device 90 or central computing system 78 can send the request for delivery of the medicine via the network 20 to another central computing system 78, for instance a central computing system 78 of another medical professional 24 or a third party 26.

The sensor system 88 of the mobile computing device 90 can detect that a medical device or instrument is being used in a medical procedure. The mobile computing device 90, another computing device 76, or the central computing system 78, and thus the system 101, can make a comparison of the detected medical device or instrument to a plurality of medical devices or instruments stored in the memory 82, such as in the database 30. Based on the comparison, the mobile computing device 90, another computing device 76, or the central computing system 78 can determine an identifier associated with the medical device or instrument. Alternatively, or additionally, the sensor system 88 of the mobile computing device 90 can detect, as described above, that a particular medical procedure is being performed.

In some cases, the medical procedure is a preparation procedure for a medical procedure that requires one or more medical devices or instruments. In such a case, the mobile computing device 90 or central computing system 78 can, based on detecting the preparation procedure, determine and indicate a respective identifier of the medical devices or instruments required for the medical procedure. The identifier can include a name of the medical device or instrument, a part number of the medical device or instrument, or the like. Based on the identifier associated with the medical device or instrument, the central computing system 78 or the mobile computing device 90, and thus the system 101, can retrieve, for instance from the memory 82 such as the database 30, instructions associated with the using the medical device or instrument.

Further, based on the identifier, the central computing system 78 or mobile computing device 90 can determine a location of the corresponding medical device or instrument in inventory. By way of example, the central computing system 78 or mobile computing device 90 can look up a given medical device in the memory 82 based on the identifier, and retrieve a location of the medical device in inventory from the memory 82. Similarly, another third party 26, such as a medical sales representative or hospital distribution center, can receive the identifier of the medical device from the mobile computing device 90 via the network 20, and can locate the medical device. For instance, inventory information can be stored in one or more databases. The database 30 or other central computing system 78 can send a message to the mobile computing device 90 that informs the mobile computing device 90 of the location of the required medical device. In response, the mobile computing device 90 can provide instructions, for instance audio or graphics, which guide the medical professional 22 in retrieving the medical device from inventory.

The central computing system 78 or mobile computing device 90 can additionally, or alternatively, assist in inventory control of medicine, medical devices or instruments, or the like. In an example, the system 101 can determine whether at least one, for instance all, medical devices or medicine required for a particular procedure are in stock in inventory. This determination can be based on at least one rule set that pertains to replenishment in inventory of medical devices or medicine. For instance, when the sensor system 88 identifies a medicine or a medical device is being used or will be used, the mobile computing device 90 can send an identifier of the medical device or medicine to the central computing system 78. Based on the identifier, the central computing system 78 can determine whether the medical device or medicine is in stock in inventory. Similarly, another third party 26, such as a medical sales representative or hospital distribution center, can receive the identifier of the medical device or medicine from the mobile computing device 90 via the network 20, and can determine whether the medical device or medicine is in stock in inventory. The central computing system 78 can send a message to the mobile computing device 90 that informs the mobile computing device 90 that the medical device or medicine is not in stock in inventory. In response, the mobile computing device 90 can generate an alert, for instance an audible or visual alert, that the medical professional 22 that the medical device is not in stock in inventory or is below a predetermined threshold in inventory. In some examples, the alert can include instructions, for instance text or graphics, which guide the medical professional 22 in reordering the medical device or medicine. In other examples, the mobile computing device 90 or central computing system 78 can automatically reorder the medical device or medicine.

Thus, as further described herein, data related to medical procedures, such as data related to medical devices and instruments, can be tracked and managed. Further, records associated with patients and medical inventories, among others, can be properly updated and maintained, thereby limiting or eliminating costly human errors that can be common to maintaining vast medical records, and thereby decreasing the latency in performing medical procedures. The information that is rendered or received by the mobile computing device 90 can be transmitted to the central computing system 78 or other computing devices via the network 20. For instance, a second medical professional 24, an implant manufacturer 28, or another third party 26 can receive the data detected by the sensor system 88 via the network 20.

In an example embodiment, using the medical data tracking application as described herein, rule sets can be retrieved from the memory 82 of the mobile computing device 90, another computing device 76, or the central computing system 78, such as the database 30. The rule sets can correspond to particular medical procedures, medical devices or instruments, medicine, patients, or the like. Alternatively, or additionally, the rule sets can be stored in memory local to the wearable device 90.

The central computing system 78 and the database 30 depicted in FIG. 2 can be operated in whole or in part by, for example, a medical device manufacturing company, a hospital, a healthcare professional, another third party, or by any combination of any of the above entities. As should be appreciated, each of the parties set forth above and/or other relevant parties may operate any number of respective computers and may communicate internally and externally using any number of networks including, for example, wide area networks (WAN's) such as the Internet or local area networks (LAN's) including wireless LAN's. Database 30 may be used, for example, to store information and rule sets for medical devices and medical device kits that are used for various medical procedures. Database 30 may also be used, for example, to store information obtained from parties such as healthcare professionals and medical device manufacturers.

It will be understood that the sensor system 88 can be configured to detect and identify any medical device or instrument as desired. Detected medical devices can include, for example, syringes, blood-pressure monitors, stethoscopes, and others. The medical devices can include medical implants such as hip implants, knee implants, shoulder implants, intervertebral implants, pedicle screws, rods, intramedullary nails, and so on. The medical devices can be configured to be implanted within a given patient.

The mobile computing device 90 can include the sensor system 88 in communication with the other computing devices. The sensor system 88 can be configured to detect the actual or physical image of objects that are within a field of view of the sensor system 88. In an example configuration, the sensor system can identify a physical object, for instance medicine, faces, hands, medical devices or instruments, or any other real-world three-dimensional object.

In an example, gestures associated with medical procedures are captured, such as via one or more cameras, image sensors, or other data capture components. The captured gestures can include one or more images, image data, and/or other motion characteristic data that identifies attributes or physical characteristics of a medical procedure. Similarly, a medical device or medicine image can be captured, such as via or one or more cameras, image sensors, or other data capture components. The medical device or medicine image can include one or more images, image data, and/or other data that identifies attributes or physical characteristics of the medical device or medicine. The image data can be analyzed, for example by one or more computer-executed data analysis processes executed by a processor of the mobile computing device 90, another computing device 76, or the central computing system 78, to determine physical characteristics of the medical device or medicine. For example, the detected image of the gestures or medical device can be analyzed by object recognition components of the central computing system 78 or the mobile computing device 90. The object recognition components can analyze physical or image data to recognize various objects, or the absence of various objects, such as various medical devices, within the field of view of the sensor system 88. Similarly, the object recognition components can analyze physical or image data to recognize various characteristics, for instance gestures, of medical procedures.

Figure 4:
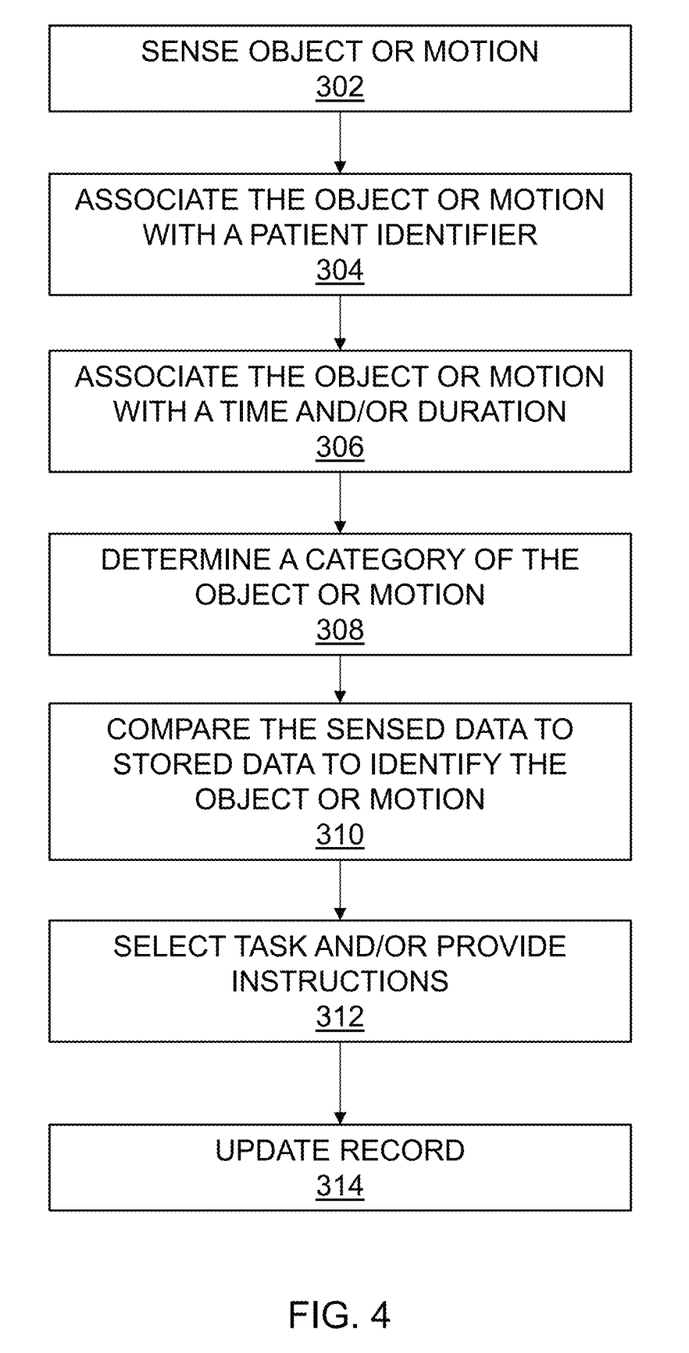
FIG. 4 is a simplified flow diagram of a method for managing and tracking medical data in accordance with an example embodiment.

Referring to FIG. 4, the steps depicted in FIG. 4 can be performed by one or more medical data tracking applications, which can be installed on a computer system that includes one or more computing devices such as a desktop, laptop, mobile phone, a wearable device, or a tablet computer. Components or computing devices within the computer system can communicate with each other via an architecture as depicted in FIG. 1 or an alternatively configured architecture as desired. In some cases, different computers and/or computing devices within a computer system may perform various different steps depicted in FIG. 4.

With continuing reference to FIG. 4, the sensor system 88 of the mobile computing device 90 detects an object or gesture, for instance a medical device, medicine, patient, or medical hand movement, at step 302. The detection can be triggered by motion of the object so as to activate the sensor system 88. In alternative embodiments, the detection can be triggered by the medical professional manually interacting with the input/output device 84 of the mobile computing device 90, such as by the medical professional activating a switch, providing an audio instruction, or making a hand gesture in front of the sensor system 88 or input device 84. In yet other embodiments, the detection can be triggered automatically by the sensor system 88. For example, the detection can be triggered by the sensor system 88 detecting a change in ambient light or by the sensor system 88 detecting that the mobile computing device 90 has entered a particular room or location using a location tracking technology such as GPS.

At step 304, the central computing system 78 or the mobile computing device 90, and thus the system 101, associates the detected object or gesture with a patient identifier that identifies the patient. The patient identifier can be a name, a number, or any combination of letters and numbers that provides a unique identification for the patient. Additionally, or alternatively, the patient identifier can be facial data or fingerprint data. The object or gesture is associated with the patient identifier so that the object or gesture can subsequently be matched with a patient record of the patient.

As step 306, the central computing system 78 or the mobile computing device 90, and thus the system 101, can associate the detected object or gesture with at least one of a time that the object or gesture is observed by the sensor system 88 and a duration over which the detected object or gesture is observed by the sensor system 88. The associated time can be used to determine when a subsequent procedure can be administered. For example, a determination as to whether to administer medication can be calculated based an amount of time that has elapsed from the associated time. The associated duration can be used, for example, to determine how long a procedure was administered.

At step 306, the central computing system 78 or the mobile computing device 90 can identify a category for the object or gesture. Example categories include medicine, medical device, gesture, patient, or the any other category related to medical data. In an example, the category can be determined based on physical characteristics of the object or gesture detected by the sensor system 88. For example, based one or more physical characteristics detected by the image sensor, the medical data tracking application, and thus the computer system, can determine that the object is a hand performing a medical procedure, a patient's face, medicine, or a medical device. Further, the medical data tracking application can determine specific parameters associated with the detected object so as that the object or medical procedure can be identified. For example, based one or more physical characteristics detected by the sensor system 88, the medical data tracking application, and thus the system 101, can determine at least one of size, shape, an amount, and color of a medical device or medicine.

Alternatively, or additionally, a category can be entered into the medical data tracking application. In some cases, a given medical device can include a device identifier, such as a serial number for instance. The device identifier can include a code, for instance a QR code, that can be scanned by the sensor system 88, or the device identifier can be alternatively entered into the medical data tracking application. The device identifier can be associated with the category. In an example configuration, the central computing system 78 or the mobile computing device 90 can classify an object by its physical attributes detected by the sensor system 88 when the object is in a field of view of the sensor system 88.

At 308, the medical data tracking application, and thus the system 101, can compare the one or more physical characteristics of the detected object or gesture to data stored in the memory 82 of the mobile computing device 90, another computing device 76, or the central computing system 78, for instance, data stored in the database 30. For instance, the physical characteristics of a detected motion or gesture can be compared to a plurality of motions, such as gestures, associated with medical procedure that are stored, so as to identify the medical procedure performed. Similarly, the physical characteristics of a detected medical device or medicine can be compared to the stored physical characteristics of medical devices or medicines, respectively, so as to identify a medical device or medicine being used or administered in a medical procedure. Further, the physical characteristics of a detected face can be compared to stored facial data that comprises the characteristics of a plurality of faces, so as to identify a patient. The category identified in step 308 can be used to narrow the search in the memory 82 to that particular category. Thus, if step 308 determines that the sensor system 88 detected an object or gesture related to a specific category, then the medical data tracking application can limit a comparison of the detected object or gesture to stored data pertaining only to that category.

In another example, by comparing the physical characteristics of the medical device to stored physical characteristics, the computer system may determine that the medical device is defective, damaged, and/or unclean. The physical characteristics can include at least one of size, shape, color, and so on.

At step 312, in accordance with the illustrated embodiment, the central computing system 78 or mobile computing device 90 can determine or select a medical procedure based on the category of the detected object, and based on the comparison of the detected object to stored data. Further, the central computing system 78 or mobile computing device 90 can determine or select at least one rule set or procedure corresponding to the identified medical procedure or patient. The rule set can be retrieved from memory 82, such as the database 30, based on the identifier of the medical device or patient and/or an identity of a medical procedure (e.g., a procedure code). In an example, the rule set can include rules pertaining to performing the medical procedure or administering a drug. For instance, the rule set can indicate the time that a given medicine was last administered or the next time that the medicine should be administered. The rule set may indicate instructions for performing a particular procedure. The rule set may provide a list of medical devices that are required to be available during a particular procedure. Such rules can guide the user or medical professional 22 in assembling a medical device kit.

By way of another example, the rule set can include rules specific to a particular patient, medicine, medical procedure, or device. For example, the rule set can include rules pertaining to physical abnormalities with a medical device, such as defects (e.g., manufacturing defects) with the medical device, or damage to the medical devices. The rule set can define a predetermined threshold associated with a physical characteristic of one or more medical devices. The physical characteristics can include at least one of size, shape, color, and so on. For instance, the predetermined threshold can stipulate permitted dimensions of a given medical device.

By way of yet another example, the rule set can include rules pertaining to instructions for performing a given medical procedure. For example, the rule set can provide instructions for administering medicine or implanting or attaching medical devices. The rule set can provide locations of medical devices so that devices can be retrieved, or the rule set can indicate which devices are required for a given medical procedure. predetermined threshold can stipulate sterile requirements of a particular medical device.

At step 312, the central computing system 78 can update a record, for instance an inventory record or patient record, based on the medical procedure that was performed. To update the inventory record or patient record, the inventory record or patient record can be identified, based on a device identifier or patient identifier, from a plurality of records stored in the database 30. The identified inventory record or patient record can then be updated to reflect the device used or the medical procedure administered. Patient records can be updated to indicate that a medical procedure was performed, a time stamp associated with the medical procedure (e.g., when the procedure was completed, how long the medical procedure took), an amount of medicine administered during the medical procedure, which devices were used during the medical procedure, and/or any issues encountered during the medical procedure. Such updates performed by the system 101 can increase efficiency and reduce human error as compared to data tracking that is not performed using the system 101.

In some examples, the user interface 86 can include a display that can include inputs, such as a touch screen for example, that provide the ability to control the system 101. Input may also be provided, for example, via other inputs of a computing device such as mouse, keyboard, camera, voice detection and the like. For example, the user can provide an input to confirm that the medical procedure, patient, or device identified by the mobile computing device 90 or central computing system 78 is correct. The user can also provide inputs to indicate that the medical procedure was performed, or to provide data related to the performed medical procedure. Alternatively, the sensor system 88 can detect that the medical procedure was performed when the medical procedure is performed within a field of view of the sensor system 88. The mobile computing device 90 can be configured to provide a location in inventory of a medical device in response to a user indicating, or the system 101 detecting, that a medical device required for a particular procedure is missing. As another example, the system 101 can be configured to provide cleaning instructions when a medical device has been identified as unclean by the system 101.

As described above, the sensor system 88 of the mobile computing device 90 can be configured to identify medical devices, medical procedures, medicines, and patients. For instance, a given medical device can be identified by a medical device identifier. A medical device identifier may be, for example, a unique identifier. However, it is not required that a medical device identifier must be a unique identifier. In some cases, a medical device identifier may be, for example, a global trade identification number (GTIN). A medical device identifier can, for example, be scanned from a bar code. A medical device identifier can also, for example, be disposed on a label of a package that contains a corresponding medical device. As another example, a medical device identifier can be etched or otherwise directly disposed on a corresponding medical device. It will be understood that a medical device identifier can be alternatively provided to the system 101 as desired.

In accordance with an example embodiment, the sensor system 88 can detect that a particular medical device a particular medical device 102 is used on a particular patient (such as, for example, in an operating room or another patient-procedure setting) as part of a particular medical procedure. By detecting use on a patient, the system 101 can identify a particular medical device that is being used on a particular patient so that, for example, the medical device can be tracked after use on the patient. Accordingly, a patient identifier can be input into or detected by the system 101. Such a patient identifier may include, for example, a name, address, insurance information and/or social security number. Information that is received by the system 101, and thus information that can be stored by the system 101, can also include, for example, an indication of a time, date, location, hospital, doctor, and other staff that may be associated with an implantation, attachment, or other use of the medical device on the patient.

As should be appreciated, some or all of the steps depicted in FIG. 4 may be repeated any number of times when, for example, additional medical tasks or procedures are performed. It will also be appreciated that various steps depicted in FIG. 4 can be omitted or performed in an order other than that shown in FIG. 4.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. For instance, the displayed visual information can include a storage object image representative of a storage object, wherein the storage object image includes a plurality of storage location areas that represent a plurality of storage locations within the storage object. The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed:

1. An employee identification card, comprising:
a card-shaped body;
an employee identifier supported by the card-shaped body, the employee identifier identifying an employee associated with the employee identification card;
a sensor system supported by the card-shaped body, the sensor system configured to detect a motion that is characteristic of a medical procedure administered to a patient and generate motion characteristic data that characterizes the medical procedure;
an output device configured to output the motion characteristic data to a central computing system that is configured to update a medical record of the patient to reflect that the procedure was administered to the patient; and a processor configured to associate the motion characteristic data with a patient identifier that identifies the patient, wherein the sensor system is configured to detect an identifying characteristic of the patient and the identifying characteristic is a face of the patient.

2. The employee identification card of claim 1, wherein the employee identifier comprises a machine-readable access code that is configured to be read by a card reader so as to grant access to an employee to a physical or virtual location.

3. The employee identification card of claim 1, wherein:
the employee identification card comprises a processor configured to associate the motion characteristic data with at least one of a time and a duration; and
the output device is configured to output the at least one of the time and duration to the central computing system.

4. The employee identification card of claim 1, wherein:
the output device is configured to output the patient identifier to the central computing system so that the central computing system can identify the medical record of the patient from a plurality of medical records of different patients stored in memory based on the patient identifier.

5. The employee identification card of claim 4, wherein:
the processor is configured to associate the motion characteristic data with the patient identifier based on the identifying characteristic.

6. The employee identification card of claim 1, wherein the sensor system comprises a dot projector configured to project infrared dots onto an object, and an infrared camera configured to read a pattern of the infrared dots to generate data corresponds to discrete points on the object.

7. The employee identification card of claim 6, wherein the sensor system comprises the dot projector, the infrared camera, a proximity sensor, an ambient light sensor, and a camera.

8. The employee identification card of claim 1, wherein:
the card-shaped body has an inner side configured to face an employee, and an outer side that is opposite the inner side along an outer direction and configured to face away from the employee; and
each sensor of the sensor system has a field of view that faces the outer direction so as to face away from the medical employee when the employee identification card is worn by an employee.

9. An electronic medical data tracking system, the system comprising:
a mobile computing device comprising a sensor system configured to detect a motion that is characteristic of a medical procedure administered to a patient, and generate motion characteristic data that characterizes the medical procedure; and
a central computing system in communication with the mobile computing device, the central computing system, comprising:
a processor; and
memory in communication with the processor, the memory having a database of patient records stored therein and instructions that, upon execution by the processor, cause the central computing system to perform operations comprising:
identifying a medical record associated with the patient from the database of patient records; and
updating the medical record associated with the patient in the database to reflect that the medical procedure has been administered to the patient, wherein at least one of the mobile computing device and the central computing system are configured to provide instructions for performing the medical procedure administered to the patient in response to the detected motion, and wherein the sensor system is configured to detect an identifying characteristic of the patient and the identifying characteristic is a face of the patient.

10. The electronic medical data tracking system of claim 9, wherein the mobile computing device is an employee identification card, comprising:
a card-shaped body that supports the sensor system;
an employee identifier supported by the card-shaped body, the employee identifier identifying an employee associated with the employee identification badge; and
an output device configured to output the motion characteristic data to the central computing system.

11. The electronic medical data tracking system of claim 9, wherein memory of at least one of the central computing system and the mobile computing device stores instructions therein that, upon execution by the central computing system or the mobile computing device, causes the central computing system or the mobile computing device to perform operations comprising;
comparing the motion characteristic data to stored data that is stored in the memory of the at least one of the central computing system and the mobile computing device; and
identifying the medical procedure based on the comparison.

12. The electronic medical data tracking system of claim 9, wherein the mobile computing device comprises:
a processor that is configured to associate the motion characteristic data with a patient identifier that identifies the patient; and
an output device that is configured to output the patient identifier to the central computing system so that the central computing system can identify the medical record associated with the patient based on the patient identifier.

13. The electronic medical data tracking system of claim 12, wherein:
the processor of at least one of the mobile computing device and the central computing system is configured to perform operations comprising:
comparing the identifying characteristic to a plurality of stored identifying characteristics that are stored in memory of at least one of the central computing system and the mobile computing device; and
associating the motion characteristic data with the patient identifier based on the comparison.

14. A computer-implemented method, comprising:
detecting, by a sensor system of a mobile computing device, a motion that is characteristic of a medical procedure administered to a patient;
generating, by the sensor system, motion characteristic data that characterizes the medical procedure;
detecting, by the sensor system, a medicine or medical device utilized in the medical procedure administered to the patient;
communicating, by the mobile computing device, the motion characteristic data to a central computing system;

detecting, by the sensor system, an identifying characteristic of the patient, wherein the identifying characteristic is a face of the patient;

identifying, by the central computing system, a medical record associated with the patient from a database of patient records stored in memory of the central computing system;

updating, by the central computing system, the medical record associated with the patient in the database based on the motion characteristic data to reflect that the medical procedure has been administered to the patient; and comparing, by at least one of the sensor system and the central computing system, an inventory level of the medicine or the medical device to a threshold level.

15. The computer-implemented method of claim 14, comprising:

comparing, by at least one of the mobile computing device and the central computing system, to the motion characteristic data to stored data that is stored in memory of the at least one of the central computing system and the mobile computing device; and identifying, by at least one of the mobile computing device and the central computing system, the medical procedure based on the comparison.

16. The computer-implemented method of claim 14, comprising:

associating, by a processor of the mobile computing device, the motion characteristic data with a patient identifier that identifies the patient; and outputting, by the mobile computing device, the patient identifier to the central computing system so that the central computing system can identify the medical record associated with the patient based on the patient identifier.

17. The computer-implemented method of claim 16, comprising:

comparing, by a processor of at least one of the mobile computing device and the central computing system, the identifying characteristic to a plurality of stored identifying characteristics that are stored in memory of at least one of the central computing system and the mobile computing device; and associating, by the processor of the at least one of the mobile computing device and the central computing system, the motion characteristic data with the patient identifier based on the comparison.

18. The computer-implemented method of claim 14, comprising at least one of:

generating, by the mobile computing device, an alert when the inventory level is less than the threshold level; and ordering, by at least one of the sensor system and the central computing system, the medicine or the medical device when the inventory level is less than the threshold level.

* * * * *